(12) United States Patent
Furuta et al.

(10) Patent No.: US 7,407,567 B2
(45) Date of Patent: Aug. 5, 2008

(54) GAS SENSOR ELEMENT AND GAS SENSOR

(75) Inventors: Nobuo Furuta, Kasugai (JP); Shigeki Mori, Seki (JP)

(73) Assignee: NGK Spark Plug Co., Ltd., Aichi (JP)

( * ) Notice: Subject to any disclaimer, the term of this patent is extended or adjusted under 35 U.S.C. 154(b) by 196 days.

(21) Appl. No.: 11/491,251

(22) Filed: Jul. 24, 2006

(65) Prior Publication Data

US 2007/0017806 A1 Jan. 25, 2007

(30) Foreign Application Priority Data

Jul. 25, 2005 (JP) ............................ P.2005-213928

(51) Int. Cl.
*G01N 27/26* (2006.01)
(52) U.S. Cl. .................. 204/426; 204/424; 204/427; 204/428; 204/429
(58) Field of Classification Search ................. 204/424, 204/426, 427, 428, 429
See application file for complete search history.

(56) References Cited

U.S. PATENT DOCUMENTS

| | | | | |
|---|---|---|---|---|
| 4,294,679 A | * | 10/1981 | Maurer et al. ............... | 204/426 |
| 4,861,456 A | * | 8/1989 | Mase et al. .................. | 204/425 |
| 6,743,352 B2 | * | 6/2004 | Ando et al. .................. | 205/781 |
| 2002/0017467 A1 | * | 2/2002 | Ando et al. .................. | 205/781 |
| 2004/0217002 A1 | * | 11/2004 | Naito et al. .................. | 204/424 |

* cited by examiner

*Primary Examiner*—Bruce F Bell
(74) *Attorney, Agent, or Firm*—Sughrue Mion, PLLC

(57) ABSTRACT

A gas sensor element including: a solid electrolyte layer having a first surface and a second surface; a first electrode formed on the first surface of the solid electrolyte layer; a second electrode formed on the second surface of the solid electrolyte layer; and an insulating layer provided between the first electrode and the first surface of the solid electrolyte layer. The insulating layer covers an outer edge of the first electrode and has an opening through which a portion of the first electrode is exposed. The opening has an area that is smaller than that of the second electrode, and is provided at a position opposite the second electrode to form a detection portion constituted by the portion of the first electrode exposed through the opening, the second electrode and the solid electrolyte layer.

9 Claims, 5 Drawing Sheets

GAS SENSOR ELEMENT AND GAS SENSOR

BACKGROUND OF THE INVENTION

1. Field of the Invention

The present invention relates to a gas sensor element and a gas sensor for detecting the concentration of a specific gas component in a gas to be measured.

2. Description of the Related Art

Known gas sensors include those for detecting the concentration of a specific gas component in a measured gas such as exhaust gas discharged from an automobile. This type of gas sensor employs a gas sensor element, the electrical characteristics of which change with the concentration of the specific gas component in the measured gas. This gas sensor element is provided with a solid electrolyte member, which is composed mainly of zirconia, for example. Such known gas sensor elements have an overall plate-like outer shape made by laminating one or more solid electrolyte members, electrodes, an insulating layer, a heater and the like. The heater is constituted by laminating an insulating layer, e.g., a ceramic layer composed mainly of alumina, a heating resistor and the like.

In the gas sensor element described above, one end portion (or the leading end portion) in the longitudinal direction of the plate shape is provided as a detecting portion for exposure to the gas to be measured, and the other end portion (or the rear end portion) is fixed on the main fitting. As such, known gas sensor elements (as described in JP-A-2003-294687, for example) have a reference electrode and a detecting electrode disposed on the two faces of the leading end side of the solid electrolyte member formed in a plate shape, and lead portions connected to those electrode portions which are individually formed along the longitudinal direction of the solid electrolyte member.

It is also known (as described in JP-A-2002-202280, for example) that the activation time of the gas sensor element (i.e., the time period required for the sensor to become active after starting the supply of electric power) can be shortened by setting the area of the detecting electrode 1.25 times or more than that of the reference electrode.

3. Problems to be Solved by the Invention

In the gas sensor element described above, however, due to tolerances or the like in the manufacturing process, a pair of electrode portions (e.g., the reference electrode and the detecting electrode), as formed on the surface and back of the solid electrolyte member, may be formed with a slight deviation in position from one another. If the reference electrode and the detecting electrode are formed such that their relative positions deviate, the effective area of the electrode portions which contribute to the detection of the specific gas (that is, the area of the respective electrode portions which directly oppose one another) differs for each gas sensor thus manufactured. Thus, a problem arises in that the gas sensors vary in performance from one another.

SUMMARY OF THE INVENTION

The present invention has been conceived to solve the aforementioned problems, and an object thereof is to provide a gas sensor element and a gas sensor, allowing for the same effective electrode area and to thereby obtain uniform performance among plural electrodes thus manufactured According to the invention, the above object has been achieved by providing a gas sensor element comprising: a solid electrolyte layer having a first surface and a second surface; a first electrode formed on said first surface of the solid electrolyte layer; a second electrode formed on said second surface of the solid electrolyte layer; and an insulating layer provided between said first electrode and said first surface of said solid electrolyte layer, covering an outer edge of said first electrode, wherein said insulating layer has an opening through which a portion of said first electrode is exposed, and the opening having a smaller area than an area of said second electrode and being provided at a position opposite said second electrode to form a detection portion constituted by the portion of said first electrode exposed through the opening, said second electrode and said solid electrolyte layer.

As a result, the insulating layer can restrict the effective area of the first electrode to the open area of the opening. Even if a positional deviation occurs between the first electrode and the second electrode, for example, the effective area in the paired electrode portions can be held constant so long as the opening of the insulating layer confronts the second electrode. As a result, it is possible to reduce fluctuation or scatter in performance among plural gas sensors thus manufactured.

The first electrode is preferably connected with a first lead portion which extends in the longitudinal direction of the solid electrolyte layer for outputting a signal from said first electrode, and the insulating layer is arranged between the first lead portion and the first surface of said solid electrolyte layer. If a positional deviation occurs between the first electrode and the second electrode, the effective area is changed by the overlapping portion between the first lead portion and the second electrode. As such, the performance of the gas sensors may fluctuate. Moreover, electric leakage may occur between the first lead portion and the second lead portion to be connected with the second electrode, thereby resulting in disperse performance among plural gas sensors. By interposing the insulating layer between the lead portion and the solid electrolyte layer, therefore, the change in the effective area due to overlap with the lead portion can be suppressed, and the electric leakage between the lead portions can also be prevented to suppress the scatter in performance.

Moreover, the first electrode preferably has an area smaller than that of said second electrode. As a result, the portion of the first electrode that is to be covered with the insulating layer is made smaller than the case in which the area of the first electrode is equal to or greater than that of the second electrode. That is, the portion of, the first electrode which does not contribute to the effective area of the detecting portion can be reduced to lower the material cost.

The insulating layer may cover the entire periphery of the first electrode. The first electrode may have a rectangular shape having a smaller width than that of the second electrode. In such case, the insulating layer may cover a leading end side and a rear end side of said first electrode, while exposing at least a portion of two longitudinally extending sides through the opening. Also, the portions of the two longitudinally extending sides exposed through the opening are opposed to the second electrode. In such configuration, due to the insulating layer, the effective area of the detecting portion can be kept unchanged, regardless of positional deviation in the longitudinal direction. Furthermore, by making the width of the first electrode smaller than that of the first electrode, the effective area of the detecting portion is unaffected by a positional deviation in the widthwise direction, Moreover, the first electrode is preferably a reference electrode, and the second electrode is a detecting electrode subject to exposure to the gas to be measured. The detecting electrode is exposed to the gas to be measured such that it tends to degrade earlier than the reference electrode. By forming the insulating layer on the reference electrode but not on the detecting electrode, the detecting electrode that is exposed to the gas to be measured can be made larger in area to thereby mitigate its degradation.

The invention can also be applied to a gas sensor element in which the reference electrode is made from a porous material, and where the reference electrode is covered with the solid electrolyte layer and a shielding member and formed into a self-generation type reference electrode. In such an arrangement, oxygen is pumped to the side of the reference electrode so that a reference oxygen concentration of a predetermined level is established inside the reference electrode. In this case, by reducing the effective area with the insulating layer, the time period for achieving the target reference oxygen concentration can be made shorter than in the case where no insulating layer is provided. As such, the activation time can be shortened. By making the effective area of the electrode constant, moreover, it is also possible to reduce fluctuation in the activation time.

The corners of the opening are preferably curved to have a radius of curvature R of 0.05 mm or more but 0.5 mm or less, so as to easily form an opening in the insulating layer.

Moreover, the porous protecting layer is laminated with said solid electrolyte layer so as to cover the second electrode which is to become the detecting electrode. The protecting layer is preferably larger, when projected in the direction opposed to the second electrode, than said second electrode. The second electrode may become poisoned as it is exposed to the gas to be measured. Therefore, the porous protecting layer is formed to cover and prevent the second electrode from becoming poisoned. By making the porous protecting layer larger than the second electrode, the second electrode is exposed in its entirety to the gas to be measured so as to prevent degradation in detecting precision among plural gas sensors.

Moreover, the gas sensor is constituted by assembling the gas sensor element having the aforementioned constitution in the metal shell, so that the effective area of the electrode can be made constant to provide plural gas sensors exhibiting little fluctuation in performance.

According to the gas sensor element and the gas sensor of the invention, the electrode effective area can be kept constant for each of the respective gas sensors thus manufactured, to thereby provide plural gas sensors of uniform performance.

DESCRIPTION OF REFERENCE NUMERALS

Figure 1:
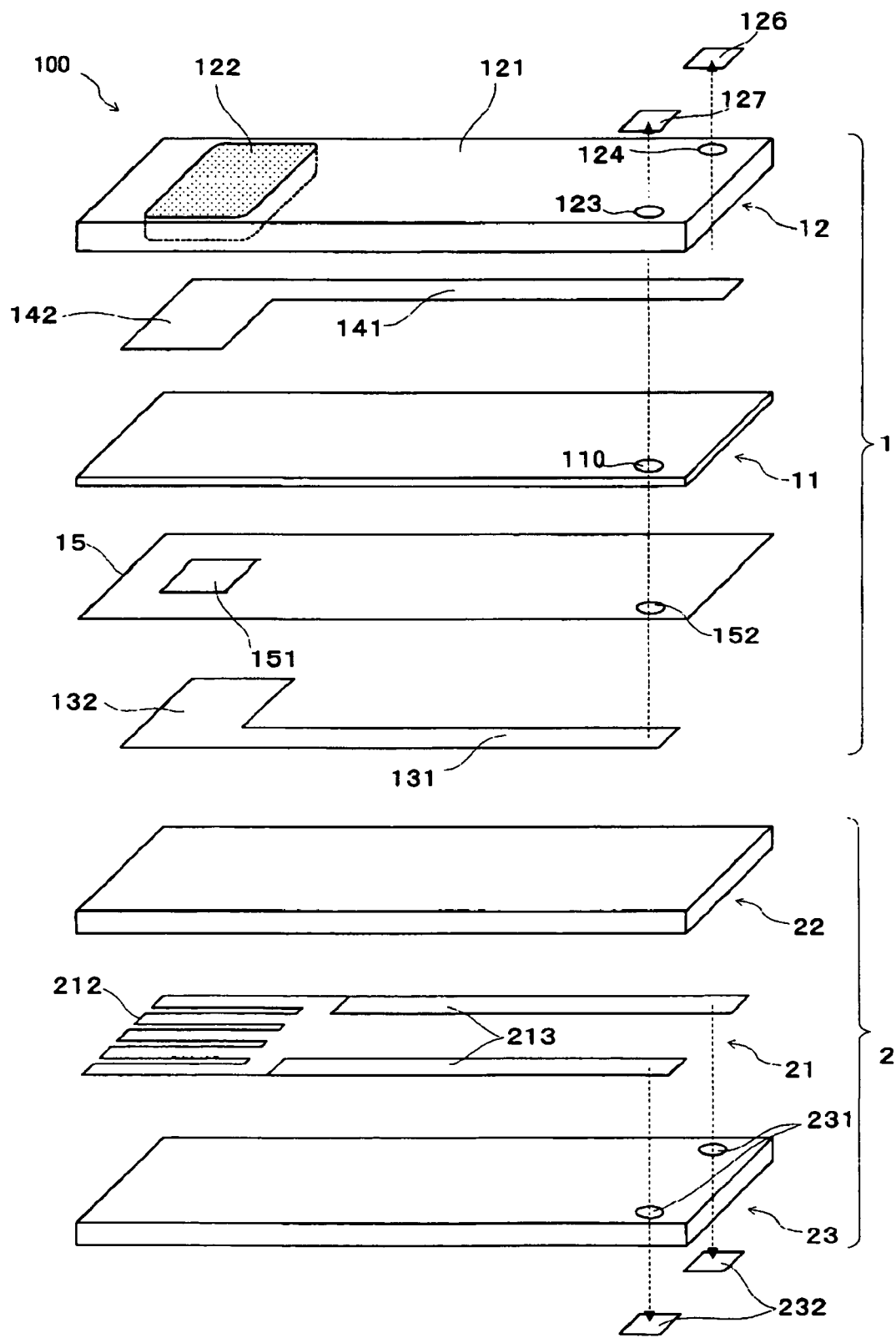
FIG. 1 is an exploded perspective view schematically showing a gas sensor element according to an embodiment of the invention.

Reference numerals used to identify various structural features in the drawings include the following.

1 - - - Gas Sensor Element Body, 2 - - - Heater, 11 - - - Solid electrolyte layer, 132 - - - Reference electrode, 142 - - - Detecting electrode, 15 - - - Insulating Layer, 100 - - - Gas Sensor Element, and 151 - - - Opening.

DETAILED DESCRIPTION OF THE INVENTION

A laminated type gas sensor element 100 according to an embodiment of the invention is described in the following with reference to the accompanying drawings. However, the present invention should not be construed as being limited thereto.

FIG. 1 is an exploded perspective view showing the structure of the gas sensor element 100 having an overall plate shape. The gas sensor element 100 comprises a laminate of a gas sensor element body 1 and a heater 2.

The gas sensor element body 1 includes a solid electrolyte layer 11 for an oxygen concentration cell, which is made from a sintered material of zirconia ($ZrO_2$) or $LaGaO_3$ containing yttria ($Y_2O_3$) or calcium oxide (CaO) as a stabilizer. In this embodiment, the zirconia solid electrolyte layer 11 can contain 10 to 80 wt. % of alumina in addition to the yttria stabilizer.

Figure 3:
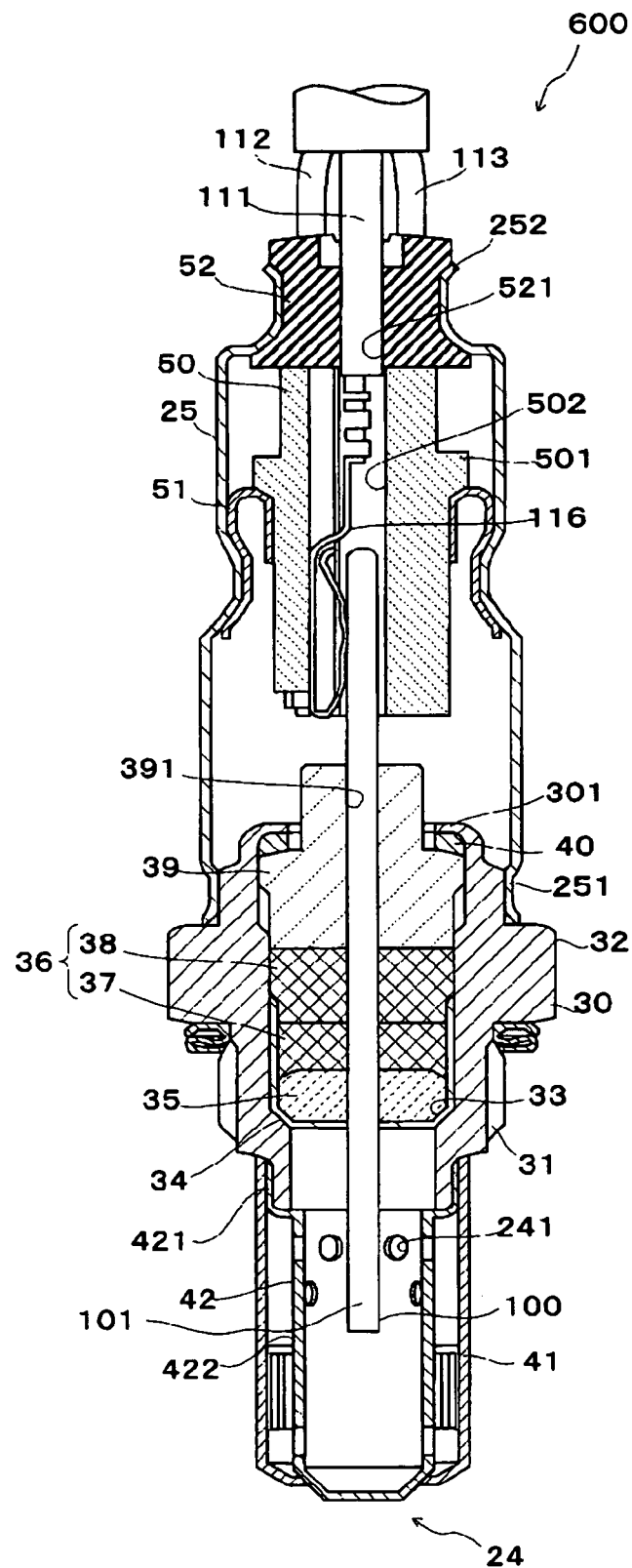
FIG. 3 is a sectional view of a gas sensor according to the embodiment of the invention.

On the side of the solid electrolyte layer 11 contacting the heater 2, a reference electrode (or a first electrode) 132 is formed, which is made from a porous material. On the side, as located on the opposite side of the reference electrode 132, of the solid electrolyte layer 11, a detecting electrode (or a second electrode) 142 is likewise formed, which is also made from a porous material. The reference electrode 132, intermediate solid electrolyte layer 11 and the detecting electrode 142 together constitute a detecting unit 101 (as shown in FIG. 3). From the reference electrode 132 and the detecting electrode 142, moreover, a first lead portion 131 and a second lead portion 141 individually extend in the longitudinal direction of the solid electrolyte layer 11. The reference electrode 132, detecting electrode 142, first lead portion 131 and second lead portion 141 are made from Pt or the like, for example. In this embodiment, the reference electrode 132 has an area of 1.6 $mm^2$, and the detecting electrode 142 has an area of 2.4 $mm^2$ smaller than that of the reference electrode 132.

An insulting layer 15 is interposed between the solid electrolyte layer 11 and the reference electrode 132 and the first lead potion 131. This insulating layer 15 has a size substantially equal to that of the solid electrolyte layer 11, and covers the outer edge of the reference electrode 132. The insulating layer 15 also has an opening 151, which is located at a position corresponding to the reference electrode 132 but which has a smaller area than the reference electrode 132. In this embodiment, the opening 151 has an area of 1.1 $mm^2$ and corners of a radius of curvature R of 0.2 mm.

By forming the insulating layer 15 covering the outer peripheral edge of the reference electrode 132, as described above, the effective area of the reference electrode 132 is limited to the area of the opening 151. As a result, the overlapping effective area of the reference electrode 132 and the detecting electrode 142 on the opposite side remains constant, even if the electrodes are misaligned. The reference electrode 132 and the opening 151 may be relatively sized such that the opening will not shift outside of the reference electrode 132 or the detecting electrode 142 even if their positional deviation is at a maximum. In an ordinary case, the positional deviation at printing is about 0.2 mm to 0.3 mm. Therefore, the aforementioned conditions are sufficiently satisfied by making the size of the opening smaller by several millimeters longitudinally and transversely than the outer size of the reference electrode 132.

By thus forming the insulating layer 15, the effective area of the paired electrode portions can be made constant to reduce variation in performance. Specifically, the constant effective area of the paired electrode portions can provide a constant output among plural sensors, and the constant resistance between the electrode portions can improve the precision in temperature control made on the basis of the resistance.

The corners of the opening are preferably curved to have a radius of curvature R of 0.05 mm to 0.5 mm so as to more easily form the opening in the insulating layer.

Moreover, the insulating layer 15 can shorten the activation time by reducing the effective area of the reference electrode 132. In the case of a self-generation type reference electrode, specifically, a pumping current is applied in a direction between the reference electrode 132 and the detecting electrode 142 such that oxygen is pumped to a reference concentration of a predetermined level in the reference electrode 132. By forming the insulating layer 15, the time period for establishing the reference oxygen concentration can be reduced to shorten the activation time. It is also possible to reduce variation in the activation time.

When the reference electrode 132 is made smaller than the detecting electrode 142 without forming the insulating layer 15, unlike the aforementioned case, it is possible to prevent fluctuation in the overlapping area due to positional deviation between the reference electrode 132 and the detecting electrode 142. However, the influence of the overlapping portions between the lead portions and the electrode becomes apparent so that the effective area cannot be made constant.

In this embodiment, the insulating layer 15 covers not only the outer peripheral edge of the reference electrode 132 but also the first lead portion 131. Even with positional deviation, therefore, the insulating layer 15 prevents the opposed area between the first lead portion 131 and the reference electrode 132 from influencing sensor performance. It is also possible to prevent electrical leakage from the first lead portion 131.

The second lead portion 141 is connected at its terminal end through a through hole 124 extending through a later-described protecting layer 12, with a signal extracting terminal 126 for connection with an external terminal. The terminal end of the first lead portion 131 is connected, through holes 110 and 152 extending through the solid electrolyte layer 11 and the insulating layer 15 and a through hole 123 extending through the protecting layer 12, with a signal extracting terminal 127 for connection with the external terminal.

Moreover, the protecting layer 12 is provided with a porous electrode protecting layer 122 formed on the surface of the detecting electrode 142 for protecting the detecting electrode 142 against poisons, and a reinforcing-protecting layer 121 formed on the surface of the second lead portion 141 for reinforcing the solid electrolyte layer 11. In this embodiment, the electrode protecting layer 122 has an area of 7.2 mm$^2$. By making the electrode protecting layer 122 larger than the detecting electrode 142, the protecting layer 122 protects the detecting electrode 142 from being exposed to measured gases and accordingly from degrading its detecting precision when employed in a gas sensor 600 (FIG. 3).

On the other hand, the heater 2 is provided with a resistance heater 21, which is clamped between a first base layer 22 and a second base layer 23 made from sintered ceramics having excellent insulation properties. The resistance heater 21 includes a heating portion 212 formed in a meandering shape, and a pair of heater lead portions 213 individually connected with the end portions of the heating portion 212 and extending in the longitudinal direction. Moreover, the end portions, located on the side opposite of the heating portion 212, of the heating portion 212 are electrically connected through two through holes 231 extending through the second base layer 23, with a pair of heater conducting terminals 232 for connection with the external terminals and in turn for connection to an external circuit.

The aforementioned first base layer 22 and second base layer 23 are made from sintered ceramics, although not especially limited, such as alumina, spinel, mullite or zirconia. These ceramics may be used individually or in combination thereof.

The resistance heater 21 may be made from a noble metal, tungsten, molybdenum or the like. Pt, Au, Ag, Pd, Ir, Ru or Rh are useful as the noble metal, of which only one or two or more kinds may be used. The resistance heater 21 is preferably made mainly of a noble metal, considering its heat resistance or oxidation resistance, and is more preferably made mainly of Pt. Moreover, the resistance heater 21 may contain a ceramic component in addition to the main noble metal. From the viewpoint of the fixing strength, the ceramic component of the resistance heater 21 is preferably the same as the main ceramic component of the first base layer 22 and that of the second base layer 23, in which the resistance heater 21 is buried.

In the resistance heater 21, moreover, the heating portion 212 generates heat when energized, but the lead portion 213 conducts an externally supplied DC voltage to the heating portion 212 but generates little heat by itself. The shapes of the heating portion 212 and lead portion 213 are not especially limited. For example, the heating portion 212 may be made thinner than the lead portion 213 such that the meandering heating portion 212 has a denser pattern than that of the lead portion 213.

On the leading end side of the gas sensor element 100 thus formed by laminating the gas sensor element body 1 and the heater 2 that is exposed to the gas to be measured, a porous protecting layer (not shown) is formed all over the circumference thereof.

FIG. 3 shows a gas sensor having the aforementioned gas sensor element 100 mounted therein, and is a sectional view showing the entirety of one example of the gas sensor 600, which is fitted to the exhaust pipe of an internal combustion engine and used for measuring the oxygen concentration in the exhaust gas.

A metal shell 30, as shown in FIG. 3, includes an externally threaded portion 31 for fitting the gas sensor to the exhaust pipe, and a hexagonal portion 32, to which a fitting tool is applied. The metal shell 30 has a fitting side step portion 33 protruding radially inward, which supports a metal holder 34 for holding the gas sensor element 100. On the inner side of the metal holder 34, moreover, a ceramic holder 35 and a talc member 36 are arranged sequentially from the leading end to thereby fix the position of the gas sensor element 100.

The talc member 36 is composed of a first talc portion 37 arranged in the metal holder 34 and a second talc portion 38 arranged to over the rear end of the metal holder 34. A sleeve 39 made from alumina is arranged on the rear end side of the second talc portion 38. The sleeve 39 is formed into a multi-stage cylindrical shape to have an axial hole 391 fitting the gas sensor element 100 therein. An additional fastening portion 301, as located on the rear end side of the metal shell 30, is bent inward, and the sleeve 39 is pushed onto the leading end side of the metal shell 30 through a ring member 40 made from stainless steel.

A metallic protector 24 is welded to the outer circumference of the leading end side of the metal shell 30. The metallic protector 24 covers the leading end portion of the gas sensor element 100 protruding from the leading end of the metal shell 30 and is provided with a plurality of gas inlet holes 241. The protector 24 has a dual structure, the outer side of which is an outer protector 41 of a bottomed cylindrical shape having a uniform outer diameter. The inner side of the protector 24 is an inner protector 42 of a bottomed cylindrical shape, which has a larger diameter at its rear end portion 421 than at its leading end portion 422.

On the other hand, an outer cylinder 25 is inserted at its leading end side onto the rear end side of the metal shell 30. This outer cylinder 25 is fixed by laser-welding a radially enlarged leading end portion 251 to the metal shell 30. Inside of the rear end side of the outer cylinder 25, a holding member 51 is interposed in the clearance between the separator 50 and the outer cylinder 25. The holding member 51 engages with a protruding portion 501 of the separator 50, as described hereinafter, so that it is fixed by the outer cylinder 25 and the separator 50 by additionally fastening the outer cylinder 25.

A through hole 502 extends in and through the separator 50, and is formed from the leading end side to the rear end side so as to accommodate lead wires 111 to 114 of the gas sensor element 100 (lead wire 114 is not shown). The through hole 502 houses a connecting terminal 116 which connects the lead wires 111 to 114 and the external terminal of the gas sensor element 100. The individual lead wires 111 to 114 are connected with a connector (not shown) external to the sensor. This connector inputs/outputs electric signals therethrough between an external device such as an ECU and the individual lead wires. Moreover, each of the lead wires 111 to 114 has a structure, in which a conductor is coated with an insulating sheath of a resin, although not specifically shown.

On the rear end side of the separator 50, a substantially cylindrical rubber cap 52 is arranged for sealing an opening 252 on the rear end side of the outer cylinder 25. The rubber cap 52 is fixed in the outer cylinder 25 by additionally fastening the outer circumference of the outer cylinder 25 radially inward while the rubber cap 52 is mounted in the rear end of the outer cylinder 25. In and through this rubber cap 52, a through hole 521 is also formed, which extends from the leading end side to the rear end side for inserting the lead wires 111 to 114.

According to the gas sensor 600 in which the gas sensor element 100 thus constituted is assembled, the effective area of the detecting electrode 142 can be maintained constant to reduce variation in performance among plural sensors. In short, the effective area of the detecting electrode 142 is made constant to provide substantially the same output for a given gas component concentration among plural sensors. Moreover, the resistance between the detecting electrode 142 and the reference electrode 132 can be fixed to a constant value among plural sensors so as to improve precision or controlling on the basis of the resistance. Moreover, it is possible to shorten the activation time and to also reduce fluctuation in the activation time.

Figure 4:
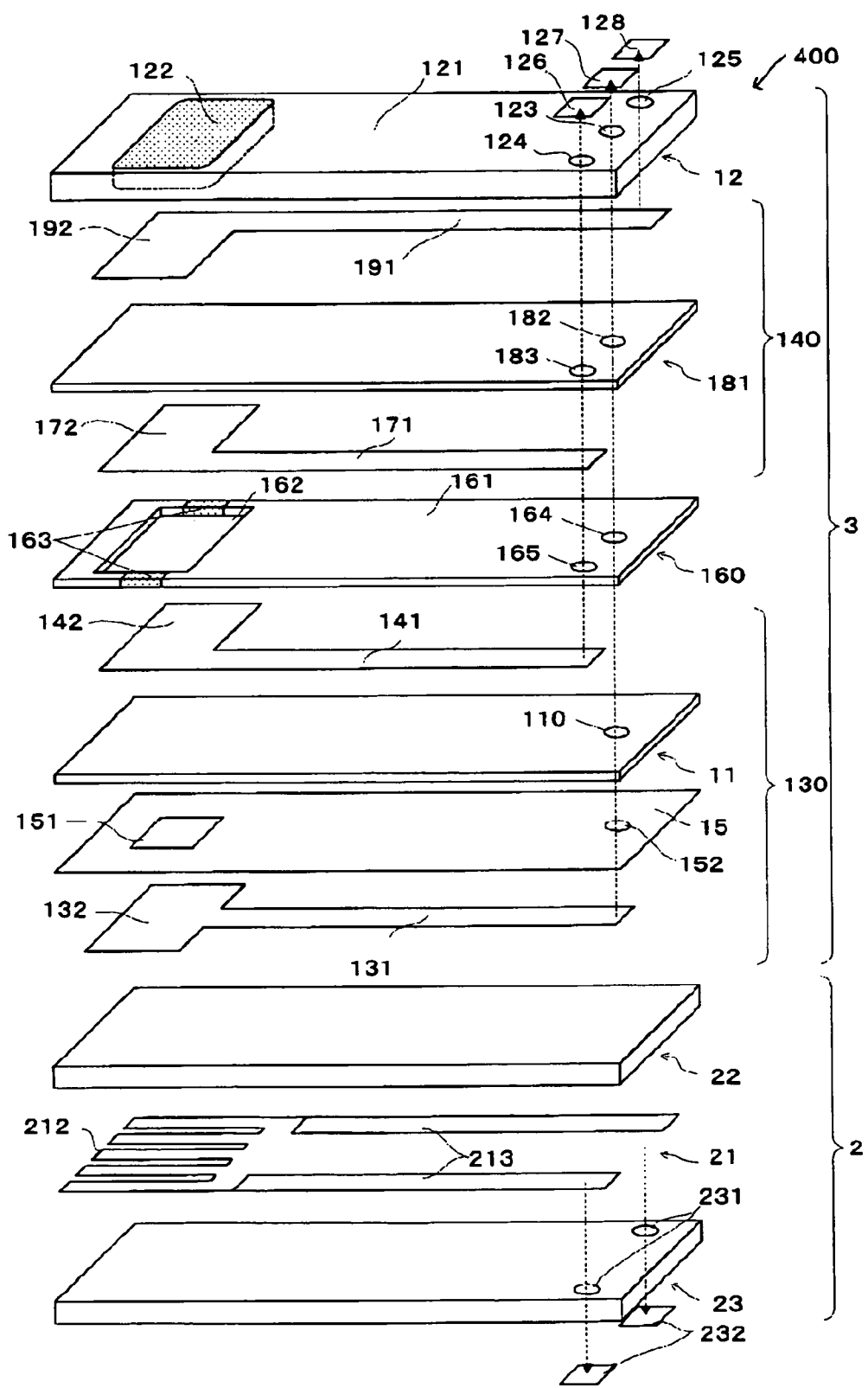
FIG. 4 is an exploded perspective view schematically showing a gas sensor element according to another embodiment of the invention.

FIG. 4 shows the constitution of a gas sensor element 400 according to another embodiment, but omits overlapping description of corresponding portions of the aforementioned gas sensor element 100, as shown in FIG. 1, designated by common reference numerals. The gas sensor element 400 of this embodiment constitutes a laminate of the heater 2 and a gas sensor element body 3.

The gas sensor element body 3 is provided with an oxygen concentration detecting cell 130 and an oxygen pump cell 140. A gas detecting chamber forming layer 160 is interposed between the oxygen concentration detecting cell 130 and the oxygen pump cell 140, and a protecting layer 12 is disposed on the outer side (on the upper side, as shown) of the oxygen pump cell 140.

The oxygen concentration detecting cell 130 is provided with solid electrolyte layer 11, and the reference electrode 132 and the detecting electrode 142 formed on the two faces of the solid electrolyte layer 11. An insulating layer 15 similar to the aforementioned one is formed between the solid electrolyte layer 11 and the reference electrode 132.

On the other hand, the oxygen pump cell 140 is provided with a second solid electrolyte layer 181, and third electrode portion 172 and fourth electrode portion 192 formed on the two faces of the second solid electrolyte layer 181. The third electrode portion 172 and the fourth electrode portion 192 constitute a detection unit together with the second solid electrolyte layer 181. The third electrode portion 172 is provided with a third lead portion 171 extending longitudinally along the second solid electrolyte layer 181. The fourth electrode portion 192 is provided with a fourth lead portion 191 extending longitudinally along the second solid electrolyte layer 181.

The gas detecting chamber forming layer 160, as formed between the oxygen pump cell 140 and the oxygen concentration detecting cell 130, is composed of an insulating portion 161 and a diffusion rate determining portion 163. In the insulating portion 161 of the gas detecting chamber forming layer 160, a gas detecting chamber 162 is formed at a position corresponding to the detecting electrode 142 and the third electrode portion 172. The gas detecting chamber 162 communicates in the widthwise direction of the gas detecting chamber forming layer 160 with the outside atmosphere. In that communicating portion, the diffusion rate determining portion 163 is arranged to realize a gas diffusion between the outside and the gas detecting chamber 162 under a predetermined rate determining condition.

The insulating portion 161 is made from sintered ceramics having insulating properties, or ceramics of an oxide group such as alumina or mullite, although not especially limited. The diffusion rate determining portion 163 is made from a porous member of alumina. The flow speed, at which the gas to be detected flows into the gas detecting chamber 162, is determined by the diffusion rate determining portion 163.

The rear end of the first lead portion 131 is electrically connected with the signal extracting terminal 127 through the through holes 110 and 152 formed in the solid electrolyte layer 11 and the insulating layer 15, a through hole 164 formed in the insulating layer 160, a through hole 182 formed in the second solid electrolyte layer 181 and the through hole 123 formed in the protecting layer 12. The rear end of the second lead portion 141 is electrically connected with the signal extracting terminal 126 through a through hole 165 formed in the insulating layer 160, a through hole 183 formed in the second solid electrolyte layer 181, and the through hole 124 formed in the protecting layer 12.

Moreover, the rear end of the third lead portion 171 is electrically connected with the signal extracting terminal 126 through the through hole 183 formed in the second solid electrolyte layer 181, and the through hole 124 formed in the protecting layer 12. The rear end of the fourth lead portion 191 is electrically connected with one signal extracting terminal 128 through a through hole 125 formed in the protecting layer 12. Here, the second lead portion 141 and the third lead portion 171 are set at the same potential through the through hole 165.

As described hereinbefore, the gas sensor element 400 having the oxygen pump cell 140 and the oxygen concentration detecting cell 130 can extract and introduce oxygen contained in the measured gas into the gas detecting chamber 162 by the oxygen pumping action of the oxygen pump cell 140, and can measure the oxygen concentration by the concentration cell action of the oxygen concentration detecting cell 130. Thus, the gas sensor element 400 can be used as an air/fuel ratio sensor or the like. As in the aforementioned case of the gas sensor element 100, the invention can be applied to the gas sensor element 400 with similar effect.

Figure 2:
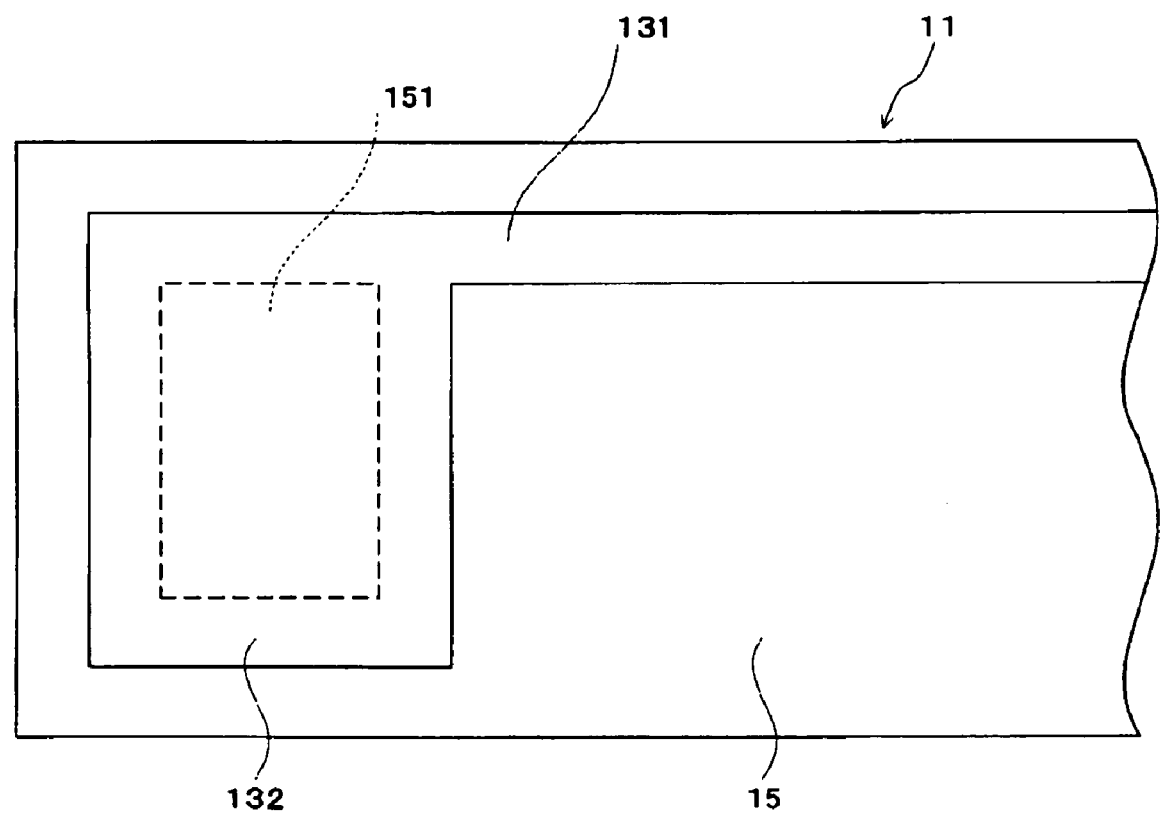
FIG. 2 is a view, as taken from an electrode portion 132 to a solid electrolyte layer 11, of the gas sensor element of FIG. 1.
Figure 5:
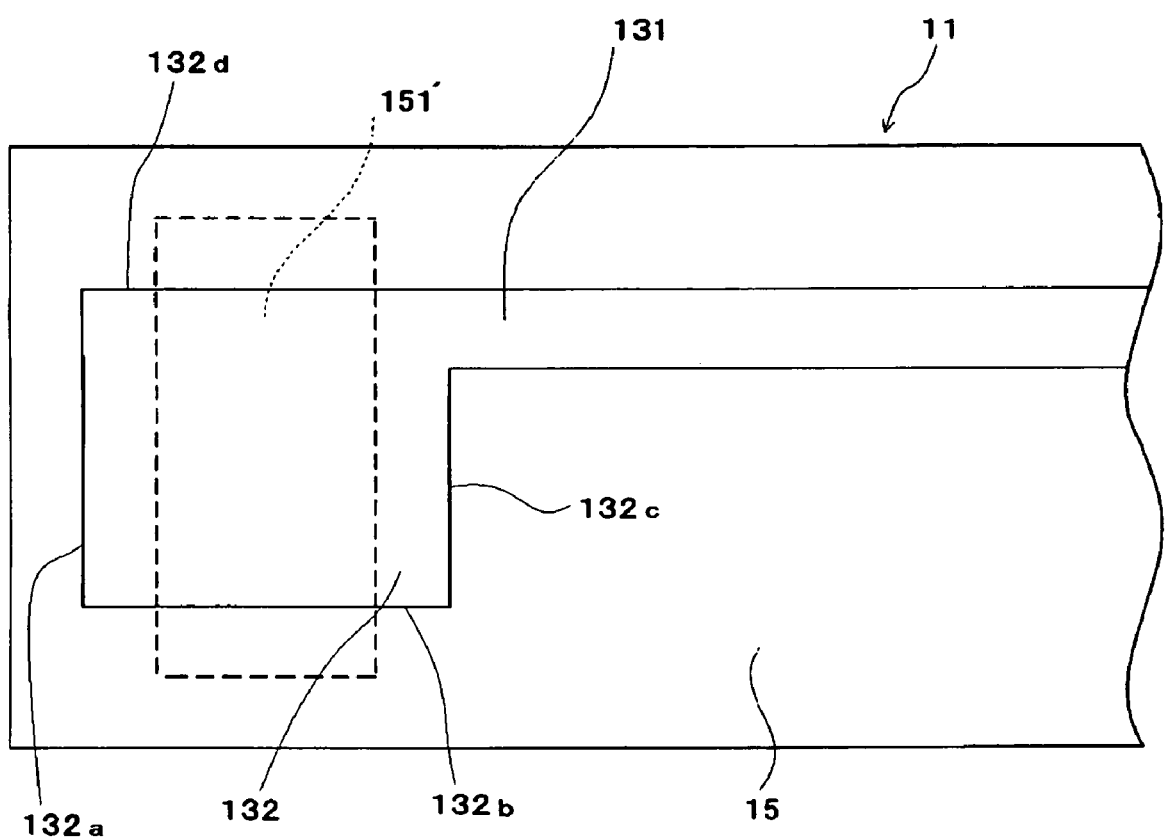
FIG. 5 is a diagram showing a modification of FIG. 2.

In FIG. 2, the insulating layer 15 is formed to cover the entirety of the outer periphery of the reference electrode 132. As shown in FIG. 5, the insulating layer 15 or rather the opening 151' can be modified such that the insulating layer 15 covers only the leading end side 132a and the rear end side 132c of the four sides (the leading end side 132a, the rear end side 132c, and one pair of sides 132b and 132d) of the rectangular reference electrode 132, but such that the paired sides 132b and 132d are exposed at least at their central portions. Thus, the leading end side 132a and the rear end side 132c are covered with the insulating layer 15. Even if, therefore, a positional deviation between the reference electrode 132 and the detecting electrode 142 occurs in the longitudinal direction, the reference electrode 132 is restricted by an opening 151' so that the effective area at the detecting portion can be kept constant.

Moreover, the paired sides 132b and 132d are designed such that they are positioned, when projected, in the area of the detecting electrode 141. Specifically, the width (i.e., the distance between the sides 132b and 132d) of the reference electrode 132 is set narrower than that of the detecting electrode 142 opposed to the reference electrode 132. Even if, therefore, a positional deviation occurs in the transverse direction, the width of the reference electrode 132 is smaller than that of the detecting electrode 142 so that the effective area at the detecting portion can be kept constant.

Since the first lead portion is covered with the insulating layer 15, moreover, the first lead portion and the detecting electrode 142 are not opposed to one another so as not to influence the effective area.

Comparing to the embodiment shown in FIG. 2, the area of the reference electrode can be reduced in the modified embodiment shown in FIG. 5 so that the cost of the noble metal material for the reference electrode can be reduced.

Although the invention has been described with respect to the above embodiments, the invention should not be construed as being limited thereto and can be suitably modified within the spirit and scope of the invention.

For example, in FIG. 4, the insulating layer 15 is not formed in the oxygen pump cell 140. The invention should not be limited thereto, but an insulating layer having an opening may be arranged between the second solid electrolyte layer 181 and the third electrode portion 172 or between the second solid electrolyte layer 181 and the fourth electrode portion 192. For example, the invention can also be applied to a laminated type gas sensor element, which is used in a gas sensor other than an oxygen sensor or an air/fuel ratio sensor, such as a HC sensor, a CO sensor or a NOx sensor.

This application is based on Japanese Patent Application JP 2005-213928, filed Jul. 25, 2005, the entire content of which is hereby incorporated by reference, the same as if set forth at length.

What is claimed is:

1. A gas sensor element comprising:
   a solid electrolyte layer having a first surface and a second surface;
   a first electrode formed on said first surface of the solid electrolyte layer;
   a second electrode formed on said second surface of the solid electrolyte layer; and
   an insulating layer provided between said first electrode and said first surface of said solid electrolyte layer, covering an outer edge of said first electrode;
   wherein said insulating layer has an opening through which a portion of said first electrode is exposed; and
   said opening having a smaller area than an area of said second electrode and being provided at a position opposite said second electrode to form a detection portion constituted by the portion of said first electrode exposed through the opening, said second electrode and said solid electrolyte layer.

2. The gas sensor element as claimed in claim 1, further comprising a first lead portion connected to said first electrode and extending in a longitudinal direction of said solid electrolyte layer, wherein said insulating layer is arranged between said first lead portion and said first surface of said solid electrolyte layer.

3. The gas sensor element as claimed in claim 1, wherein said first electrode has an area smaller than that of said second electrode.

4. The gas sensor element as claimed in claim 1, wherein said insulating layer covers the entire periphery of said first electrode.

5. The gas sensor element as claimed in claim 1, wherein:
   said first electrode has a rectangular shape including a first opposing pair of leading end and rear end sides and a second opposing pair of longitudinally extending sides, said first electrode having a width smaller than that of said second electrode;
   said insulating layer covering the leading end and rear end sides of said first electrode, and at least a portion of each of said two longitudinally extending sides of said first electrode is exposed through said opening; and
   said portions of said two longitudinally extending sides exposed through said opening are opposed to said second electrode.

6. The gas sensor element as claimed in claim 1, wherein:
   said first electrode is a reference electrode; and
   said second electrode is a detecting electrode subject to exposure to said gas to be measured.

7. The gas sensor element as claimed in claim 6, wherein:
   said reference electrode is made from a porous material; and
   said reference electrode is covered with said solid electrolyte layer and a shielding member and is a self-generating reference electrode, in which oxygen is pumped on a side of said reference electrode so that a reference oxygen concentration of a predetermined level is established inside said reference electrode by the pumped oxygen.

8. A gas sensor comprising a metal shell and the gas sensor element as claimed in claim 1 assembled in said metal shell.

9. The gas sensor as claimed in claim 5, wherein a central portion of each of said longitudinally extending sides is exposed through said opening.

* * * * *